US00PP24616P2

(12) United States Plant Patent
Bergman

(10) Patent No.: US PP24,616 P2
(45) Date of Patent: Jul. 8, 2014

(54) ***CHRYSANTHEMUM* PLANT NAMED 'CIDZ0044'**

(50) Latin Name: *Chrysanthemum×morifolium*
Varietal Denomination: CIDZ0044

(71) Applicant: Syngenta Crop Protection AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 6 days.

(21) Appl. No.: 13/694,855

(22) Filed: Jan. 11, 2013

(51) Int. Cl.
*A01H 5/00* (2006.01)

(52) U.S. Cl.
USPC ..... Plt./286

(58) Field of Classification Search
USPC ..... Plt./286, 295, 296
See application file for complete search history.

*Primary Examiner* — Anne Grunberg
(74) *Attorney, Agent, or Firm* — Joshua L. Price

(57) ABSTRACT

A new *Chrysanthemum* plant named 'CIDZ0044' particularly distinguished by the bright greyed orange and yellow ray florets on a daisy form inflorescence, with medium sized foliage with a strong and sturdy growth habit.

1 Drawing Sheet

Latin name of the genus and species of the plant claimed: *Chrysanthemum×morifolium.*

Varietal denomination: 'CIDZ0044'.

BACKGROUND OF THE NEW PLANT

The present invention comprises a new *Chrysanthemum*, botanically known as *Chrysanthemum×morifolium*, and hereinafter referred to by the variety name 'CIDZ0044'.

'CIDZ0044' is a product of a planned breeding program. The new cultivar has bright greyed orange and yellow ray florets on a daisy form inflorescence, with medium sized foliage with a strong and sturdy growth habit.

'CIDZ0044' originates as a whole plant mutation of 'CIDZ0006', U.S. Plant Pat. No. 22,955. 'CIDZ0044' was discovered and selected by the inventor as a single flowering plant within a large population of the parent cultivar, grown outdoors in a saran field Fort Myers, Fla. in November 2009. The parent cultivar 'CIDZ0006' has ray florets of a red-purple with green basal spot.

The first act of asexual reproduction of 'CIDZ0044' was accomplished when vegetative cuttings were propagated from the initial selection in January 2010 in a greenhouse in Fort Myers, Fla.

BRIEF SUMMARY OF INVENTION

Horticultural examination of plants grown from cuttings of the plant initiated in January 2010, and continuing thereafter, has demonstrated that the combination of characteristics as herein disclosed for 'CIDZ0044' are firmly fixed and are retained through successive generations of asexual reproduction.

'CIDZ0044' has not been observed under all possible environmental conditions. The phenotype may vary significantly with variations in environment such as temperature, light intensity and day length.

A Plant Breeder's Right for this cultivar was applied for in Canada on Jun. 29, 2012, (12-7648). 'CIDZ0044' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

Figure 1:
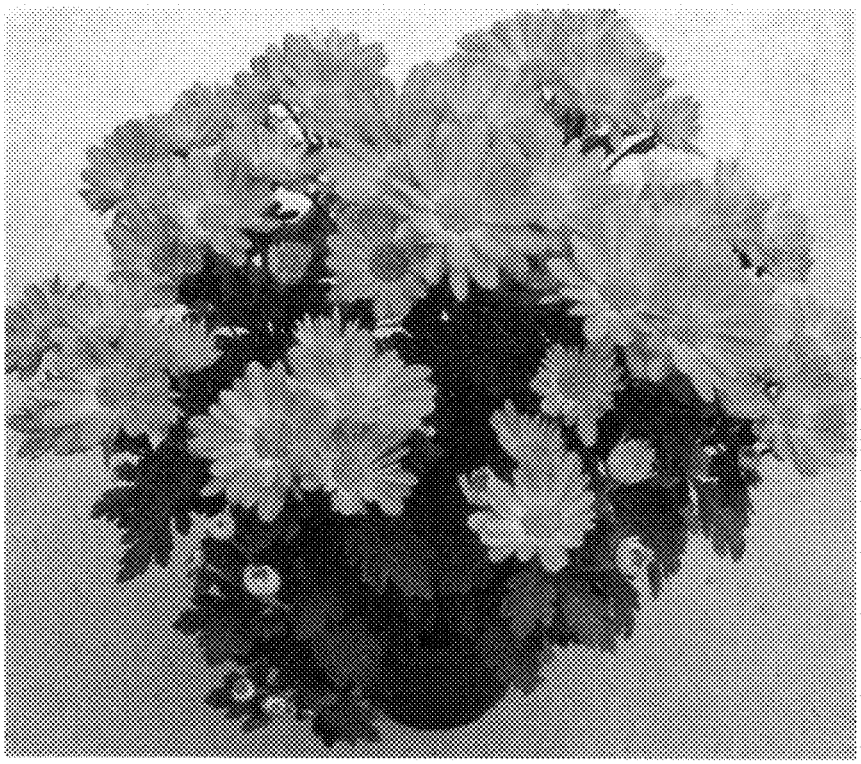
Figure 2:
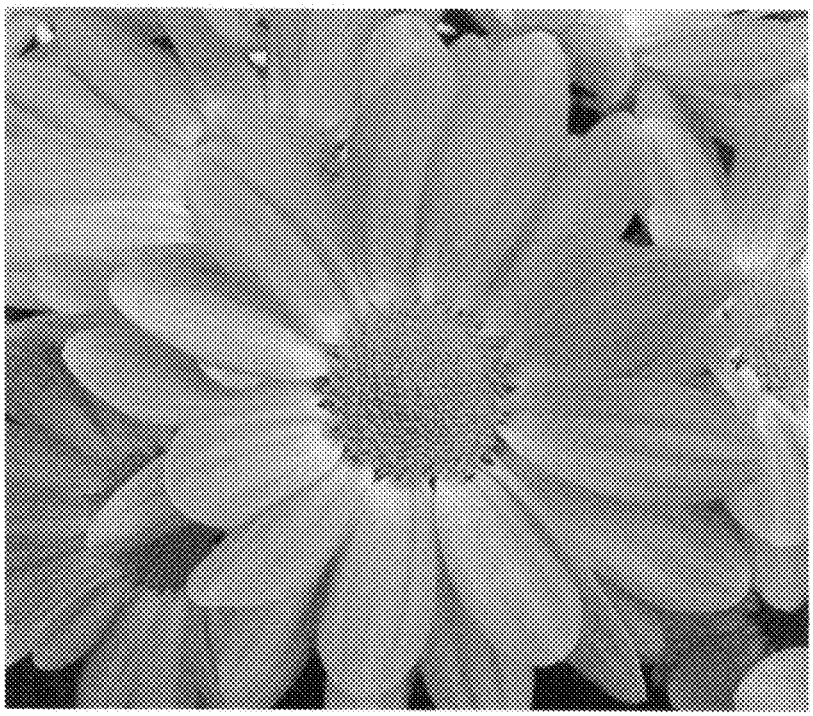

The accompanying photographic drawing shows typical flower and foliage characteristics of 'CIDZ0044' with colors being as true as possible with an illustration of this type. The photographic drawing shows in FIG. 1 four flowering plants of the new variety growing in one container, and in FIG. 2, a close-up of the inflorescences.

DETAILED BOTANICAL DESCRIPTION

The plant descriptions, measurements and aforementioned photographs were taken in Gilroy, Calif. in early October 2012 under natural light. These plants were grown 4 plants in a 6-inch container in a greenhouse in Nipomo, Calif. These plants used in the photograph and descriptions were about 10-12 weeks old.

Color references are made to The Royal Horticultural Society Colour Chart (R.H.S.) 2001.

TABLE 1

DIFFERENCES BETWEEN THE NEW VARIETY 'CIDZ0044' AND A MOST SIMILAR VARIETY (IN COLOR)

| | 'CIDZ0044' | 'Syncin Pueblo' (U.S. Plant Pat. No. 22,305) |
|---|---|---|
| Disc center dark spot: | Does not develop | Develops in center when grown cool |

TABLE 1-continued

DIFFERENCES BETWEEN THE NEW VARIETY 'CIDZ0044' AND A MOST SIMILAR VARIETY (IN COLOR)

| | 'CIDZ0044' | 'Syncin Pueblo' (U.S. Plant Pat. No. 22,305) |
|---|---|---|
| Ray floret color: | Brighter/lighter greyed orange with a yellow basal band | Darker greyed orange with no yellow band |
| Inflorescence size: | Smaller | Larger |
| Plant habit: | More compact with smaller foliage size | Larger plant habit and foliage size |

Plant:

*Form, growth and habit.*—Herbaceous, pot-type, stems upright and freely branching, strong and sturdy growth habit.

*Plant height.*—25-28.0 cm.

*Plant height (inflorescence included).*—29-33.0 cm.

*Plant width.*—18-20.0 cm.

Roots:

*Number of days to initiate roots.*—About 4 days at about 22 degrees C.

*Number of days to produce a rooted cutting.*—4-6 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 147A.

*Immature, leaf color, lower surface.*—Closest to RHS 147B.

*Mature, leaf color, upper surface.*—Lighter than RHS 147A.

*Mature, leaf color, lower surface.*—RHS 147B.

*Length.*—7.3-7.6 cm.

*Width.*—4.5-4.8 cm.

*Shape.*—Ovate.

*Base shape.*—Attenuate.

*Apex shape.*—Mucronulate.

*Margin.*—Palamtely lobed, slightly incised and dentate.

*Texture, upper surface.*—Bifid T-shaped hairs.

*Texture, lower surface.*—Bifid T-shaped hairs.

*Color of veins, upper surface.*—RHS 144B.

*Color of veins, lower surface.*—RHS 144B.

*Pattern of veining.*—Palmate.

*Petiole color.*—RHS 144B.

*Length.*—1.5 cm.

*Diameter.*—0.3 cm.

*Texture.*—Bifid T-shaped hairs.

Stem:

*Quantity of main branches per plant.*—3-6.

*Color of stem.*—RHS 138A but appears lighter due to hairs.

*Length of stem.*—23-25.0 cm.

*Diameter.*—0.4-0.5 cm.

*Length of internodes.*—0.3-0.8 cm.

*Texture.*—Bifid T-shaped hairs.

*Color of peduncle.*—RHS 138A but appears lighter due to hairs.

*Length of peduncle.*—9-11.5 cm.

*Peduncle diameter.*—0.3 cm.

*Texture.*—Bifid T-shaped hairs.

Inflorescence:

*Type.*—Compositae, solitary inflorescences borne terminally above foliage, ray florets arranged acropetally on a capitulum.

*Quantity of short days to flowering (response time).*—About 59 days.

*Natural season flowering.*—Not determined on this variety.

*Quantity of inflorescences per plant.*—10-26 with 2-16 buds.

*Lastingness of individual blooms on the plant.*—About 4 weeks.

*Fragrance.*—Slightly spicy.

Bud (just when opening/showing color):

*Color.*—RHS 6C with RHS 9A at the apex.

*Length.*—1.5-2.1 cm.

*Width.*—1.5-1.7 cm.

*Shape.*—Oblate.

Immature inflorescence:

*Diameter.*—5.0 cm when flattened out.

*Color of ray florets, upper surface.*—Closest to RHS 2B lightly overlaid and mottled with RHS 172B.

*Color of ray florets, lower surface.*—RHS 3B.

Mature inflorescence:

*Diameter.*—7.2-7.5 cm.

*Depth.*—1.5-2.0 cm.

*Total diameter of disc.*—1.7 cm.

*Receptacle color.*—RHS 145B.

*Receptacle height.*—0.4-0.5 cm.

*Receptacle diameter.*—0.7 cm.

Ray florets:

*Average quantity of florets.*—25-27 in 2 whorls.

*Color of florets, upper surface.*—RHS 2B heavily overlaid with shades of RHS 171B to RHS N172C.

*Color of florets, lower surface.*—RHS 3B to RHS 3C.

*Length.*—2.7-3.1 cm.

*Width.*—0.9-1.15 cm.

*Shape.*—Elliptical.

*Apex shape.*—Emarginate.

*Base shape.*—Cuneate.

*Margin.*—Entire.

*Texture, upper surface.*—Papillose.

*Texture, lower surface.*—Papillose.

Disc florets:

*Average quantity of florets.*—About 500.

*Color of florets.*—RHS 7B with RHS 4C basally and RHS 145A very apex on very immature.

*Length.*—0.5 cm.

*Width.*—0.1 cm.

*Shape.*—Tubular, elongated.

*Apex shape.*—Acute, 5 pointed.

*Texture, inner surface.*—Glabrous.

*Texture, outer surface.*—Glabrous.

Phyllaries:

*Quantity.*—About 30.

*Color, upper surface.*—RHS 138B.

*Color, lower surface.*—RHS 138B.

*Length.*—0.7-1.0 cm.

*Width.*—0.1-0.15 cm.

*Shape.*—Lanceolate.

*Apex shape.*—Acute.

*Base.*—Fused.

*Margins.*—Entire.

*Texture, upper surface.*—Glabrous.

*Texture, lower surface.*—Bifid T-shaped hairs.

Reproductive organs:

*Pistil.*—1, found on both types of florets.
*Length.*—0.5-0.6 cm.
*Style color*.—RHS 1B to RHS 1C.
*Style length.*—0.45-0.55 cm.
*Stigma color*.—RHS 3A.
*Stigma shape*.—Bi-parted.
*Ovary color*.—RHS 155C.
*Ovary length.*—0.1 cm.
*Ovary width.*—0.1 cm.
*Stamens.*—4, found on only on the disc florets.
*Color of filaments*.—RHS 1C.
*Length filaments.*—0.2 cm.
*Anther color*.—RHS 14C.
*Anther length.*—0.2 cm.
*Anther shape*.—Oblong.
*Color of pollen*.—RHS 15A.
*Pollen amount*.—Scarce.
*Fertility/seed set*.—Has not been observed to date.
*Disease/pest resistance*.—Has not been observed to date.

What is claimed is:

1. A new and distinct variety of *Chrysanthemum* plant named 'CIDZ0044' substantially as illustrated and described herein.

* * * * *